(12) United States Patent
Liu

(10) Patent No.: US 11,219,502 B2
(45) Date of Patent: Jan. 11, 2022

(54) TRANSFORMATIVE SHAPE-MEMORY POLYMER TISSUE CAVITY MARKER DEVICES, SYSTEMS AND DEPLOYMENT METHODS

(71) Applicant: Medtronic Advanced Energy, LLC, Minneapolis, MN (US)

(72) Inventor: Yisi Liu, Winchester, MA (US)

(73) Assignee: Medtronic Advanced Energy, LLC, Minneapolis, MN (US)

( * ) Notice: Subject to any disclaimer, the term of this patent is extended or adjusted under 35 U.S.C. 154(b) by 561 days.

(21) Appl. No.: 16/033,694

(22) Filed: Jul. 12, 2018

(65) Prior Publication Data
US 2019/0076212 A1  Mar. 14, 2019

Related U.S. Application Data

(60) Provisional application No. 62/556,669, filed on Sep. 11, 2017.

(51) Int. Cl.
  *A61B 6/00* (2006.01)
  *A61B 90/00* (2016.01)
  *A61B 17/00* (2006.01)

(52) U.S. Cl.
  CPC .... *A61B 90/39* (2016.02); *A61B 2017/00004* (2013.01); *A61B 2017/00867* (2013.01); *A61B 2017/00871* (2013.01); *A61B 2090/3908* (2016.02); *A61B 2090/3912* (2016.02); *A61B 2090/3962* (2016.02); *A61B 2090/3966* (2016.02); *A61B 2090/3987* (2016.02)

(58) Field of Classification Search
  CPC .................................................. A61B 90/039
  See application file for complete search history.

(56) References Cited

U.S. PATENT DOCUMENTS

| 3,157,524 A | 11/1964 | Artandi |
| 3,520,402 A | 7/1970 | Nichols et al. |
| 4,832,686 A | 5/1989 | Anderson |
| 4,957,479 A | 9/1990 | Roemer |
| 5,019,087 A | 5/1991 | Nichols |
| 5,429,582 A | 7/1995 | Williams |
| 5,607,477 A | 3/1997 | Schindler et al. |

(Continued)

OTHER PUBLICATIONS

U.S. Appl. No. 16/033,836, filed Jul. 12, 2018, First named inventor: Yisi Liu.

*Primary Examiner* — Joel F Brutus
(74) *Attorney, Agent, or Firm* — Patterson Thuente Pedersen, P.A.

(57) ABSTRACT

Embodiments relate to transformative shape-memory polymer tissue cavity markers and corresponding systems and deployment methods. In one embodiment, a tissue cavity marker for delivery to a tissue cavity via a minimally invasive surgical incision includes a transformative body having a first three-dimensional shape in a permanent state and a second three-dimensional shape different from the first three-dimensional shape in a temporary state, the transformative body comprising a shape-memory polymer material and being automatically transformable between the temporary state for delivery to a tissue cavity and the permanent state for residence within the tissue cavity by application of a stimulus; and at least one radiopaque marker coupled to the transformative body.

24 Claims, 5 Drawing Sheets

(56) References Cited

U.S. PATENT DOCUMENTS

| | | |
|---|---|---|
| 5,676,146 A | 10/1997 | Scarborough |
| 5,716,404 A | 2/1998 | Vacanti et al. |
| 5,873,865 A | 2/1999 | Horzewski et al. |
| 6,030,333 A | 2/2000 | Sioshansi et al. |
| 6,071,301 A | 6/2000 | Cragg et al. |
| 6,161,034 A | 12/2000 | Burbank et al. |
| 6,228,055 B1 | 5/2001 | Foerster et al. |
| 6,270,464 B1 | 8/2001 | Fulton, III et al. |
| 6,340,367 B1 | 1/2002 | Stinson et al. |
| 6,477,423 B1 | 11/2002 | Jenkins |
| 6,579,310 B1 | 6/2003 | Cox et al. |
| 6,699,205 B2 | 3/2004 | Fulton, III et al. |
| 6,725,083 B1 | 4/2004 | Burbank et al. |
| 7,047,063 B2 | 5/2006 | Burbank et al. |
| 7,229,417 B2 | 6/2007 | Foerster et al. |
| 7,524,274 B2 | 4/2009 | Patrick et al. |
| 7,547,274 B2 | 6/2009 | Rapach et al. |
| 7,875,059 B2 | 1/2011 | Patterson et al. |
| 7,972,261 B2 | 5/2011 | Lamoureux et al. |
| 8,052,658 B2 | 11/2011 | Field |
| 8,060,183 B2 | 11/2011 | Leopold et al. |
| 8,157,862 B2 | 4/2012 | Corbitt, Jr. et al. |
| 8,486,028 B2 | 7/2013 | Field |
| 9,014,787 B2 | 4/2015 | Stubbs et al. |
| 9,199,092 B2 | 12/2015 | Stubbs et al. |
| 9,386,942 B2 | 7/2016 | Chi Sing et al. |
| 9,615,915 B2 | 4/2017 | Lebovic et al. |
| 2001/0034528 A1 | 10/2001 | Foerster et al. |
| 2001/0041936 A1 | 11/2001 | Corbitt, Jr. et al. |
| 2001/0047164 A1 | 11/2001 | Teague et al. |
| 2002/0072806 A1 | 6/2002 | Buskirk et al. |
| 2003/0083732 A1 | 5/2003 | Stinson |
| 2004/0124105 A1* | 7/2004 | Seiler ............... A61B 90/39 206/363 |
| 2004/0249457 A1 | 12/2004 | Smith et al. |
| 2005/0049489 A1 | 3/2005 | Foerster et al. |
| 2005/0074405 A1 | 4/2005 | Williams, III |
| 2005/0080338 A1 | 4/2005 | Sirimanne et al. |
| 2005/0080339 A1 | 4/2005 | Sirimanne et al. |
| 2005/0101860 A1 | 5/2005 | Patrick et al. |
| 2005/0143770 A1 | 6/2005 | Carter et al. |
| 2005/0165480 A1 | 7/2005 | Jordan et al. |
| 2005/0234336 A1 | 10/2005 | Beckman et al. |
| 2006/0025795 A1 | 2/2006 | Chesbrough et al. |
| 2006/0058570 A1 | 3/2006 | Rapach et al. |
| 2006/0116713 A1 | 6/2006 | Sepetka et al. |
| 2006/0173296 A1 | 8/2006 | Miller et al. |
| 2007/0021642 A1 | 1/2007 | Lamoureux et al. |
| 2007/0032703 A1* | 2/2007 | Sankaran ........... A61B 17/3439 600/208 |
| 2007/0038014 A1 | 2/2007 | Cox et al. |
| 2007/0038017 A1 | 2/2007 | Chu |
| 2007/0167668 A1 | 7/2007 | White et al. |
| 2008/0015472 A1 | 1/2008 | Ressemann et al. |
| 2008/0045773 A1 | 2/2008 | Popowski et al. |
| 2008/0097199 A1 | 4/2008 | Mullen |
| 2008/0228164 A1 | 9/2008 | Nicoson et al. |
| 2008/0243226 A1 | 10/2008 | Fernandez et al. |
| 2008/0269603 A1* | 10/2008 | Nicoson ................ A61B 90/39 600/431 |
| 2008/0281388 A1 | 11/2008 | Corbitt et al. |
| 2009/0024225 A1 | 1/2009 | Stubbs et al. |
| 2009/0030298 A1 | 1/2009 | Matthews et al. |
| 2009/0143747 A1 | 6/2009 | Dias et al. |
| 2009/0319046 A1 | 12/2009 | Krespi et al. |
| 2010/0010341 A1 | 1/2010 | Talpade et al. |
| 2010/0030072 A1 | 2/2010 | Casanova et al. |
| 2010/0042104 A1 | 2/2010 | Kota et al. |
| 2010/0234726 A1* | 9/2010 | Sirimanne ........... A61K 49/006 600/426 |
| 2010/0312272 A1* | 12/2010 | Pavcnik ............. A61B 17/0057 606/213 |
| 2011/0004094 A1 | 1/2011 | Subbs et al. |
| 2011/0028831 A1 | 2/2011 | Kent |
| 2011/0130655 A1 | 6/2011 | Nielson et al. |
| 2011/0313288 A1 | 12/2011 | Chi Sing et al. |
| 2013/0032962 A1 | 2/2013 | Liu et al. |
| 2013/0289390 A1 | 10/2013 | Herman et al. |
| 2013/0317275 A1 | 11/2013 | Stubbs |
| 2015/0112194 A1 | 4/2015 | Stubbs |
| 2015/0297316 A1* | 10/2015 | Grinstaff ................ A61B 10/04 600/414 |
| 2016/0082286 A1 | 3/2016 | Stubbs et al. |

\* cited by examiner

TRANSFORMATIVE SHAPE-MEMORY POLYMER TISSUE CAVITY MARKER DEVICES, SYSTEMS AND DEPLOYMENT METHODS

PRIORITY

This application claims the benefit of and priority to U.S. Provisional Application No. 62/556,669, filed Sep. 11, 2017, the entire contents of which is incorporated herein by reference.

TECHNICAL FIELD

This disclosure relates generally to tissue markers and more particularly to transformative shape-memory polymer tissue cavity markers and corresponding systems and deployment methods.

BACKGROUND

Treatment of breast and other cancers often involves a biopsy, lumpectomy, or tumor or tissue resection. Many of these procedures now can be performed using minimally invasive procedures, such as by forming a small incision through which a biopsy tool or device can be inserted and removed. Minimally invasive procedures can be more comfortable and provide quicker healing for patients than open surgical procedures, while at the same time being less complex to perform.

After a biopsy, lumpectomy or resection procedure to remove tissue, localized radiation therapy can be provided to treat tissue remaining proximate the procedure area (e.g., at the "margin" of the cavity created when the tissue was removed) and reduce the chance of local recurrence in cases in which the removed tissue is found to be abnormal or cancerous and some abnormal or cancerous cells may have been left behind. To provide an accurate and lasting target for radiation, or simply to mark a tissue or cavity site for monitoring or future reference even if radiation therapy is not needed, radiopaque markers can be placed at the tissue removal site. While radiopaque markers can be placed at the site immediately after the tissue is removed, conventional markers typically are small in size and therefore can migrate within the cavity created when the tissue was removed or later as new tissue grows and fills the cavity. Conventional radiopaque markers also cannot fully define or mark the walls of the cavity.

To address this, some markers are mounted on or coupled to a support structure device that more completely fills the cavity volume. These support structure devices are large, however, and cannot be delivered via the same incision used in the minimally invasive procedure to remove the tissue. Moreover, these devices can be uncomfortable for patients both as they are delivered (and removed, if they must be later) and when they are in place.

SUMMARY

Embodiments of transformative shape-memory polymer tissue cavity markers and corresponding systems and deployment methods are disclosed.

In an embodiment, tissue cavity marker for delivery to a tissue cavity via a minimally invasive surgical incision comprises a transformative body having a first three-dimensional shape in a permanent state and a second three-dimensional shape different from the first three-dimensional shape in a temporary state, the transformative body comprising a shape-memory polymer material and being automatically transformable between the temporary state for delivery to a tissue cavity and the permanent state for residence within the tissue cavity by application of a stimulus; and at least one radiopaque marker coupled to the transformative body.

In an embodiment, a tissue cavity marking system for delivering a tissue cavity marker to a tissue cavity via a minimally invasive surgical incision comprises a delivery device comprising a control mechanism at a proximal end and a tissue cavity marker aperture at a distal end, the control mechanism operable in use to deploy a tissue cavity marker from the tissue cavity marker aperture, and at least one tissue cavity marker comprising a transformative body having a first three-dimensional shape in a permanent state and a second three-dimensional shape different from the first three-dimensional shape in a temporary state, the transformative body comprising a shape-memory polymer material and being automatically transformable between the temporary state for delivery to a tissue cavity and the permanent state for residence within the tissue cavity by application of a stimulus; and at least one radiopaque marker coupled to the transformative body.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figure 1A:
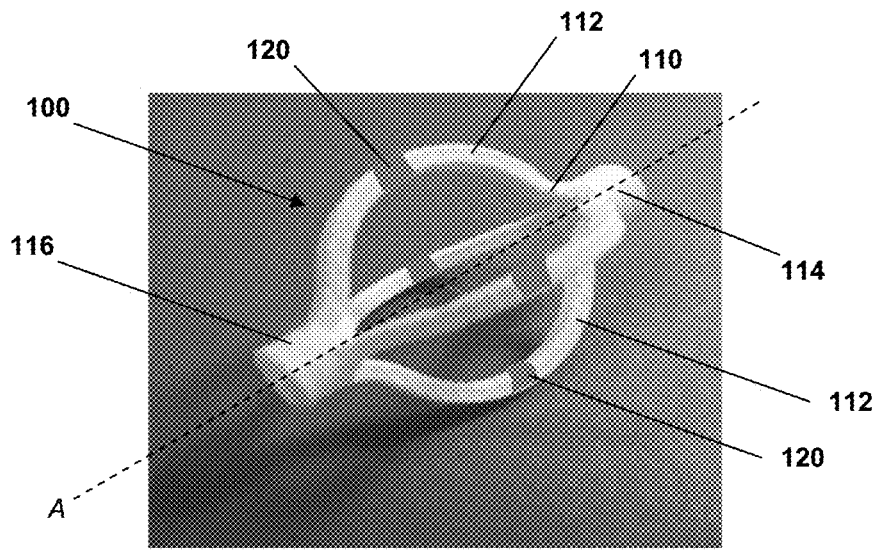
FIG. 1A depicts a shape-memory polymer tissue cavity marker in a permanent state according to an embodiment.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Embodiments relate to transformative shape-memory polymer tissue cavity markers and corresponding systems and deployment methods. In one embodiment, a shape-memory polymer tissue cavity marker comprises a shape-memory polymer material structure and at least one radiopaque marker element coupled with the shape-memory polymer material structure. The shape memory polymer material enables the tissue cavity marker to transform between a temporary state, in which a profile or dimension of the tissue cavity marker is reduced such that the tissue cavity marker can be deployed through a minimally invasive surgical procedure incision, and a permanent state, in which a profile or dimension of the tissue cavity marker is increased such that the tissue cavity marker fills or defines a volume of a tissue cavity.

Embodiments also relate to shape-memory polymer tissue cavity marker deployment devices and systems. In one embodiment, a deployment device comprises a catheter, syringe or other tool having a proximal (operator) end and a distal (patient) end. The proximal end comprises a control mechanism by which the deployment device can be operated during use. The distal end comprises an aperture into which a shape-memory polymer tissue cavity marker in the temporary state can be loaded. The distal end can be inserted through a minimally invasive surgical incision to deliver the tissue cavity marker to a target site. At the target site, the control mechanism can be used to deploy and release the tissue cavity marker from the deployment device. As it is being deployed, or after it has been deployed, the tissue cavity marker can be transitioned to the permanent state, such as by using the deployment device; using a separate device, tool or material; by body temperature within the tissue cavity; or without further active intervention.

Throughout this disclosure, some like elements are referenced similarly, iterated by factors of 100 (e.g., 100 and 200 each refer to tissue cavity markers but of different configurations). Additionally, the drawings are not necessarily to scale, and the relative shapes and sizes of various components in some embodiments may not be exactly as depicted.

Figure 1B:
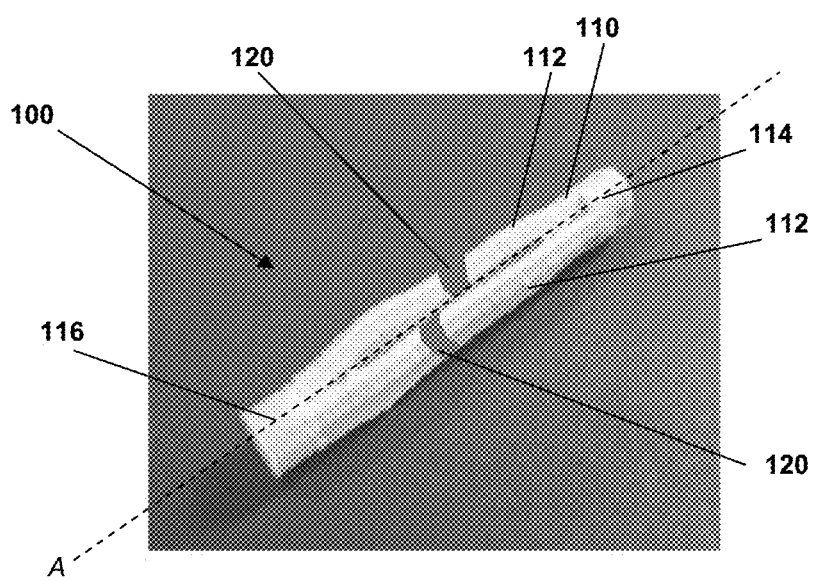
FIG. 1B depicts the shape-memory polymer tissue cavity marker of FIG. 1A in a temporary state.

Referring to FIGS. 1A and 1B, one embodiment of a shape-memory polymer tissue cavity marker 100 is depicted. Tissue cavity marker 100 comprises a transformative body 110 and at least one radiopaque marker 120 coupled with transformative body 110.

Though the particular configuration can vary in embodiments, transformative body 110 is generally of a size, three-dimensional shape, and sufficient rigidity to be deployed and maintain (for some amount of time) a structural configuration within a tissue cavity created by a biopsy, lumpectomy or other resection of tissue. For example, transformative body 110 or tissue cavity marker 100 overall can have a compressed diameter in its delivery or temporary state (permanent and temporary states are discussed in more detail below) of about 10 millimeters (mm) or less, such as about 8 mm or less, about 7 mm or less, about 6 mm or less, or about 5 mm or less, in various embodiments. In its deployed or permanent state, transformative body 110 or tissue cavity marker 100 overall can have a diameter of about 10 mm or more, such as about 15 mm or more, about 20 mm or more, about 25 mm or more, or about 30 mm or more, in various embodiments. A range of diameters of transformative body 110 or tissue cavity marker 100 overall in the deployed or permanent state is about 10 mm to about 30 mm in one example.

Transformative body 110 of tissue cavity marker 100 can comprise a variety of different three-dimensional shapes in a permanent state (permanent and temporary states are discussed below) in various embodiments, such as the generally spherical cage-like configuration shown in FIG. 1A. In FIG. 1A, transformative body 110 comprises a plurality of spaced-apart branches 112 coupled together by first and second end portions 114 and 116. In other similar embodiments, a number or relative arrangement of branches 112 can vary, such that transformative body 110 comprises more or fewer branches 112 spaced closer together or farther apart from one another, or differently sized from one another. Additionally, first and second end portions 114 and 116 can have other shapes or configurations or be omitted in other embodiments.

In other embodiments, transformative body 110 can comprise a helix (see, e.g., tissue cavity marker 200 of FIGS. 2A and 2B), spiral, spheroid, ellipsoid, ovoid, cylinder, cuboid, cone, triangular prism, pyramid, or some other three-dimensional shape, including a combination of two or more of these shapes. A particular tissue cavity size, configuration, patient anatomy or type (e.g., human adult, human pediatric, veterinary), deployment device or situation, or other characteristic may benefit from a custom shape, which can be created in some embodiments. For example, tissue cavity marker 100 is sized and shaped for residence in a tissue cavity and can be sized and shaped so as to just fit within a particular cavity or to be slightly compressed when installed in and restrained by the tissue surrounding the cavity. In at least this sense, tissue cavity marker 100 can physically interact with at least a portion of a margin of the cavity in which it is deployed.

Transformative body 110 comprises a shape-memory material in embodiments, such as a shape-memory polymer. Shape-memory polymers are polymeric "smart" materials that have the ability to transition between a first three-dimensional shape in a permanent state and a second three-dimensional shape different from the first three-dimensional shape in a temporary state when induced to do so by an external stimulus or trigger. A first three-dimensional shape in a permanent state of tissue cavity marker 100 is depicted in FIG. 1A, and a second three-dimensional shape different from the first three-dimensional shape in a temporary state of tissue cavity marker 100 is depicted in FIG. 1B. In this disclosure, the permanent state of tissue cavity marker 100 is the state or configuration of tissue cavity marker 100 when it is deployed and resident in a tissue cavity, while the temporary state of tissue cavity marker 100 is a state that enables at least one dimension (e.g., a diameter, radius, width or volume) but sometimes two or all three dimensions of tissue cavity marker 100 to be temporarily reduced in order to enable or ease delivery and deployment of tissue cavity marker 100 in a tissue cavity via a minimally invasive surgical incision. For example, in one embodiment at least two dimensions of tissue cavity marker 100 in its permanent state are greater than a length of a minimally invasive surgical incision, but in its temporary state these dimensions are reduced such that tissue cavity marker 100 can be delivered via the minimally invasive surgical incision. Minimally invasive surgical incisions can be about 3 centimeters (cm) long or less, such as about 2 cm long or less, or about 1 cm long or less, or less than about 7 mm long, for example about 6 mm long in one example. A range of minimally invasive surgical incision lengths is between 5 mm and 1 cm in one example. From the temporary state, the shape-memory polymer material of transformative body 110 will cause transformative body 110 to automatically return to the permanent state when induced to do so by the appropriate external stimulus or trigger. Some shape-memory polymers referred to as triple-shape-memory polymers also have a third state (for example, a first temporary state, a second temporary state, and a permanent state) and can have applicability in some embodiments of tissue cavity marker 100. Though the permanent and temporary states are used as discussed above herein, they also can be reversed, such that tissue cavity marker 100 is in a temporary state when resident in a tissue cavity and a permanent state when being delivered to the tissue cavity.

The permanent state can be influenced by or depend upon the shape and configuration of transformative body 110. For example, the spherical cage-like configuration of FIG. 1A enables radial expansion and compression of transformative body 110 as branches 112 move toward or away from a central axis A that extends lengthwise through tissue cavity marker 100 from end portion 114 to end portion 116. As branches 112 radially expand or compress, end portions 114 and 116 move toward or away from one another along axis A. As such, both the diameter and length of transformative body 110 change between the permanent and temporary states of tissue cavity marker 100. Other shapes will exhibit other changes in transition between expanded and compressed/contracted states. Tissue cavity marker 200 of FIGS. 2A and 2B, for example, transitions between a permanent helical state depicted in FIG. 2A and a temporary extended state depicted in FIG. 2B.

The permanent state of tissue cavity marker 100 is a "memory" state, in that the shape-memory polymer material of transformative body 110 is programmed to assume a particular permanent state shape. This programming can be done as part of the manufacturing process and involve, e.g., thermodynamic strain and stress locking processing, or other processes according to the particular external stimulus to which the shape-memory polymer is responsive. A similar programming can be performed for the temporary state, as well as for a third state in embodiments in which one is used, such that the various states of tissue cavity marker 100 are predefined according to material properties of transformative body 110.

The external stimulus or trigger that causes a shape-memory polymer material to transition between permanent and temporary states can be a temperature change (e.g., heating or cooling the material), photo-illumination (e.g., exposing the material to different wavelengths of light), electro-activation, or some other stimulus. The same external stimulus or trigger can cause the material to transition both from the permanent state to the temporary state, and from the temporary state to the permanent state. Example shape-memory polymers that can be suitable for use in embodiments of tissue cavity marker 100 include those that are biodegradable or bioabsorbable (also referred to as resorbable), and those that are homopolymers, copolymers or terpolymers. Some suitable examples include poly-lactic acid (PLA), poly-L-lactide (PLLA), poly-L-glycolic acid (PLGA), polycaprolactone (PCL), and PLA-, PLGA- and PCL-based materials. In some embodiments, combinations of one or more of these or other suitable shape-memory polymers can be used, with particular combinations selected to achieve particular shape-memory effects or responses. Other suitable biodegradable polymers and other shape-memory polymer materials will be recognized by those of ordinary skill in the art. In certain embodiments, non-bioabsorbable shape-memory polymers or other materials can be used, in addition to or instead of the aforementioned bioabsorbable materials. The terms polymers and shape-memory polymers generally are used herein and can include any of these materials or formulations.

Tissue cavity marker devices formed from shape-memory polymer materials can be distinguished from other materials or devices, such as mechanical springs that can be compressed or stretched from a resting position but require constant applied force to remain stretched or compressed (depending upon their resting spring state). Some medical devices, such as stents, rely on spring-like properties when they are mechanically compressed in order to be loaded into and delivered by a catheter, and they return to their resting position when the compression is removed or released. Other devices have a compressed resting position that requires controlled mechanical force once delivered (e.g., via a balloon catheter or saline injection) in order to be expanded. None of these devices, however, can automatically and repeatedly transition between permanent and temporary states, and remain in either the permanent or temporary state, without an external mechanical force continuously acting on the device to maintain it in at least one of the states.

Tissue cavity marker 100 can additionally or instead comprise a shape-memory alloy material, such as Nitinol. Shape-memory alloys are not bioabsorbable but may have application in some procedures or situations in which bioabsorbability of some or all of transformative body 110 is not desired or required. For example, in one embodiment at least one marker 120 coupled to transformative body 110 comprises a shape-memory alloy, while transformative body 110 comprises a shape-memory polymer.

Generally, however, markers 120 comprise a radiopaque material without shape-memory transition properties. Radiopaque materials are those that are opaque to and therefore visible on X-ray or other radiation images. Examples of radiopaque materials include metals (e.g., titanium, nonferromagnetic stainless steel) as well as some plastics and polymers known to those of ordinary skill in the art. Including radiopaque markers 120 on transformative body 110 of tissue cavity marker 100 makes it possible to locate markers 120 (and thereby the cavity in which tissue cavity marker 100 is resident) on radiation images after tissue cavity marker 100 is deployed in the cavity, including after transformative body 110 is resorbed. This can be helpful for follow-up treatments (e.g., targeted radiation therapy) and ongoing monitoring of the cavity and tissue margins of the cavity.

The number, size and relative arrangement of markers 120 can vary from those depicted in FIGS. 1A and 1B. For example, end portions 114 and 116 also can comprise one or more markers 120 in embodiments. In other embodiments, some markers 120 may be smaller, larger, or differently shaped than other markers 120. The permanent and temporary states of tissue cavity marker 100 can be considered when arranging a plurality of markers 120 thereon. For example, two markers 120 can be staggered such that when tissue cavity marker 100 is in the temporary state of FIG. 1B adjacent markers 120 do not align in ways that interfere with one another and a profile of tissue cavity marker 100 can still be sufficiently reduced to be loaded into a deployment device and delivered by a minimally invasive surgical incision.

Structurally, markers 120 can comprise clips that are coupled to transformative body 110. This coupling can be accomplished in a variety of ways, such as by folding, wrapping, crimping or otherwise forming a length of material around a portion (e.g., a branch 112 or end portion 114, 116) of transformative body 110. In other embodiments, markers 120 can be coupled with transformative body 110 by being at least partially embedded or formed therein. In still other embodiments, transformative body 110 can be formed in or on one or more markers 120, such as by being injection-molded through a marker 120 that comprises a ring, tube or other structure that is hollow or comprises an aperture through which a portion of transformative body 110 can pass. In further embodiments, one or both of transformative body 110 and markers 120 can be three-dimensionally printed, together or separately.

Figure 2A:
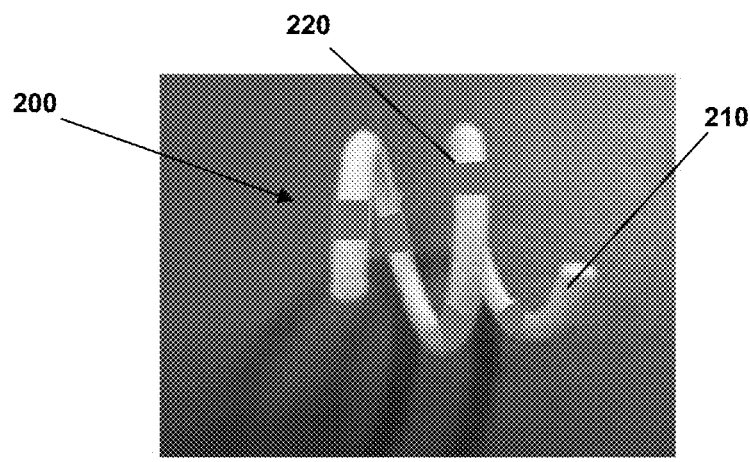
FIG. 2A depicts a shape-memory polymer tissue cavity marker in a permanent state according to an embodiment.
Figure 2B:
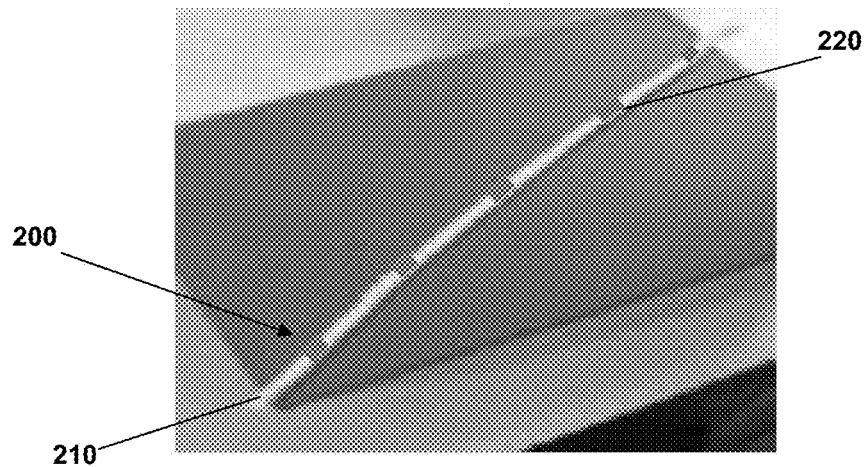
FIG. 2B depicts the shape-memory polymer tissue cavity marker of FIG. 2A in a temporary state.

Referring to FIGS. 2A and 2B, tissue cavity marker 200 comprises a transformative body 210 and at least one marker 220 coupled to transformative body 210. As previously mentioned, transformative body 210 has a helical configuration in its permanent state (FIG. 2A) and an extended configuration in its temporary state (FIG. 2B). The materials, behaviors and other characteristics of tissue cavity marker 200, transformative body 210 and markers 220 are similar to or the same as those discussed above with respect to tissue cavity marker 100, transformative body 110 and markers 120, though one difference is that the diameter of tissue cavity marker 200 in its temporary state is smaller than that of tissue cavity marker 100 in its temporary state, such that tissue cavity marker 200 can be delivered via even smaller incisions.

Figure 3A:
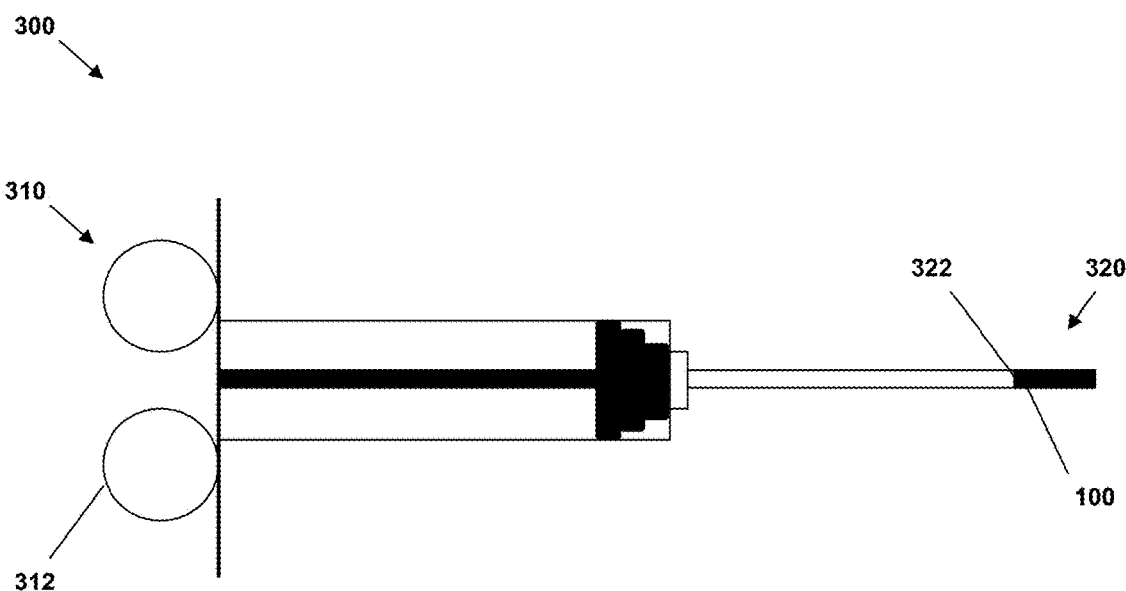
FIG. 3A depicts a delivery device loaded with a shape-memory polymer tissue cavity marker according to an embodiment.
Figure 3B:
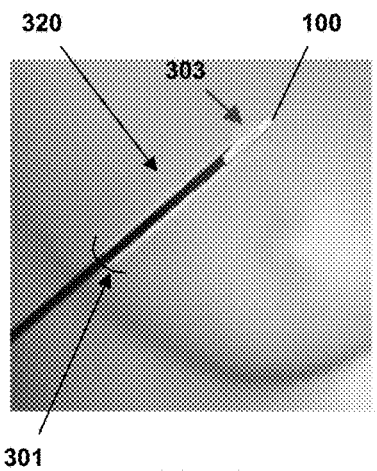
FIG. 3B depicts a distal portion of a delivery device delivering a shape-memory polymer tissue cavity marker to a tissue cavity according to an embodiment.
Figure 3C:
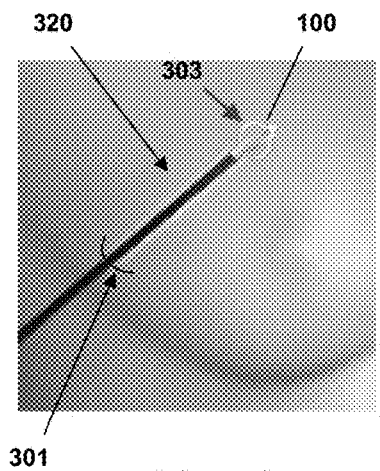
FIG. 3C depicts a distal portion of a delivery device delivering a heated fluid to the shape-memory polymer tissue cavity marker and tissue cavity of FIG. 3B.

Referring to FIGS. 3A, 3B and 3C, and returning to the example embodiment of tissue cavity marker 100 of FIGS. 1A and 1B, a delivery device 300 is depicted. Delivery device 300 comprises a proximal control end 310 and a distal delivery end 320. Here and throughout, "proximal" is used with respect to an operator/physician end (310) of delivery device 300, and "distal" is used with respect to a patient or delivery end (320) of delivery device 300.

Delivery device 300 can comprise a catheter, syringe or other device into which a tissue cavity marker (e.g., tissue cavity marker 100) can be loaded in its temporary state, delivered to a cavity site via a minimally invasive surgical incision, deployed within the cavity, and transitioned from the temporary state to the permanent state. In some embodiments, the transition from temporary to permanent state of tissue cavity marker 100 can be accomplished using at least one additional tool or device.

Proximal control end 310 of delivery device 300 comprises a control system 312 via which delivery device 300 can be controlled. In particular, control system 312 allows an operator of delivery device 300 to manipulate delivery device 300 to insert distal delivery end 320 through an incision, guide distal delivery end 320 to a delivery site (such as a tissue cavity), and control deployment of tissue cavity marker 100 from distal delivery end 320 to the delivery site. Control system 312 can comprise one or more of a plunger (depicted in FIG. 3A), guidewire, mechanical actuator, robotic or computer-assisted control mechanism, or some other control mechanism that can be manipulated in order to control delivery device 300 and effect delivery and deployment of tissue cavity marker 100.

Distal delivery end 320 comprises a distal end aperture 322 into which tissue cavity marker 100 can be loaded. In some embodiments, distal end aperture 322 can comprise or be part of a cannula, trocar, catheter or other hollow device forming part or all of distal delivery end 320 or delivery device 300. Though many different configurations and types of devices can be used in various embodiments, they will be generally referred to herein, inclusively, as delivery device 300 and distal delivery end 320. Distal delivery end 320 can be rigid or flexible, and straight, curved or angled, in various embodiments. In some particular embodiments, a first portion of distal delivery end 320 can be rigid, and a second portion of distal delivery end 320 can be flexible. Similarly, a first portion of distal delivery end 320 can be straight, and a second portion of distal delivery end 320 can be curved. At least a portion of distal delivery end 320 being rigid can be advantageous in some embodiments to assist an operator in manipulating delivery device 300 to maneuver tissue cavity marker 100 into place in a tissue cavity, though some operators may prefer a degree of flexibility.

In FIG. 3A, tissue cavity marker 100 (in its temporary state) is loaded into distal end aperture 322. One tissue cavity marker 100 can be loaded into distal end aperture 322, or multiple tissue cavity markers 100 can be loaded into distal end aperture 322, such as in a case in which multiple tissue cavities of a single patient are to be marked. In some embodiments, tissue cavity marker 100 can be preloaded into distal end aperture 322. In such an embodiment, delivery device 300 can be provided in sterile packaging and need only be removed from the packaging by a physician or other medical professional in order to deliver and deploy tissue cavity marker 100. In other embodiments, tissue cavity marker 100 can be provided in separate sterile packaging or in some other configuration separate from but relative to delivery device 300. For example, tissue cavity marker 100 can be provided preloaded in its temporary state in distal delivery end 320, with distal delivery end 320 provided in sterile packaging separate from proximal control portion 310 of delivery device 300, which may be sterilizable and reusable in some embodiments. Prior to use, distal delivery end 320 can be removed from its packaging, coupled with proximal control portion 310, and used to deliver and deploy tissue cavity marker 100 at a desired site.

Still other ways of providing tissue cavity marker 100 and delivery device 300 or portions thereof can be implemented in other embodiments. For example, it may be helpful to provide, separate from delivery device 300, a variety of tissue cavity markers (100, 200, etc.) from which a physician or other medical professional can select an appropriate one for any particular cavity, patient or procedure. In general, however, it can be convenient for tissue cavity marker 100 to be preloaded in delivery device 300 in its temporary state to avoid a physician having to transition tissue cavity marker 100 from its permanent state to its temporary state (e.g., by heating or cooling tissue cavity marker 100) in order to load tissue cavity marker 100 into delivery device 300. Nevertheless, there may be situations in which this is necessary or desired (e.g., according to physician preference).

Referring to FIG. 3B, delivery device 300 is depicted in use, with distal delivery end 320 inserted via an incision 301 in a patient's skin to an internal tissue cavity 303, such as one created by a breast tissue biopsy or lumpectomy. In some embodiments, tissue cavity marker 100 in its temporary state is deployed in cavity 303 from distal delivery end 320. For example, the tip of distal delivery end 320 can be advanced to a distal edge of cavity 303, and tissue cavity marker 100 can be deployed from distal end aperture 322 as distal delivery end 320 and delivery device 300 are retracted. In another example, distal delivery end 320 is advanced to a proximal edge of cavity 303, and tissue cavity marker 100 is deployed by being pushed into cavity 303, such as by control system 312. In some embodiments, image-guided surgical techniques can be used to view distal delivery end 320 as it is directed to and within cavity 303 and ensure tissue cavity marker 100 is placed within cavity 303 prior to or after deployment of tissue cavity marker 100 from delivery device 300. In these embodiments, delivery device 300 can comprise a colorant, radiopaque or radiographic filler, or other additive in or coating on distal delivery end 320 to aid in visualization or navigation.

Figure 3D:
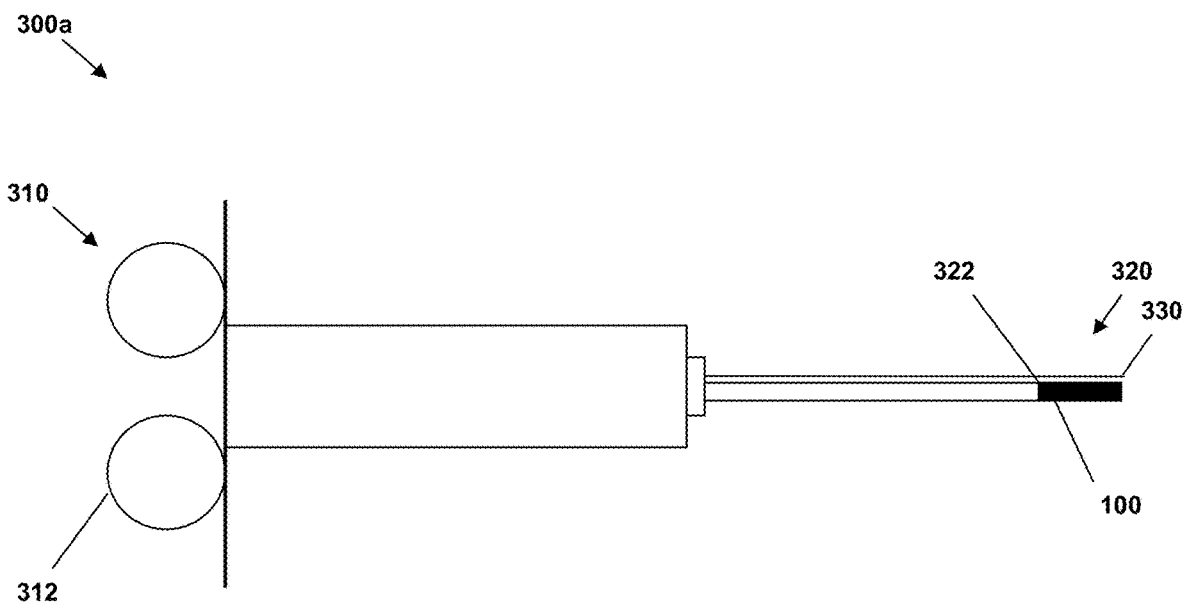
FIG. 3D depicts a delivery device loaded with a shape-memory polymer tissue cavity marker according to another embodiment.

Referring to FIG. 3C, tissue cavity marker 100 is transitioned to its permanent state within cavity 303. In the embodiment of FIG. 3C, this is accomplished by injecting a heated liquid, such as saline, into cavity 303 via a fluid aperture 330 (see delivery device 300a of FIG. 3D) in distal delivery end 320. The temperature of the heated liquid can vary according to a temperature necessary to cause a particular shape-memory polymer material of tissue cavity marker 100 to transition to its permanent state.

In some embodiments, this temperature is higher than human body temperature, such as higher than about 37 degrees Celsius, for example higher than 40 degrees Celsius, higher than 50 degrees Celsius, higher than 60 degrees Celsius, or higher than 70 degrees Celsius. The temperature also can be less than 100 degrees Celsius, less than 90 degrees Celsius, less than 80 degrees Celsius, less than 70 degrees Celsius, less than 60 degrees Celsius, or less than 50 degrees Celsius. In some embodiments, the temperature of the liquid is between 40 degrees Celsius and 90 degrees Celsius, for example between 60 degrees Celsius and 80 degrees Celsius.

In other embodiments, this temperature is lower than human body temperature, such that it is a cooled rather than heated liquid that is delivered, again according to the properties of the particular shape-memory polymer material of tissue cavity marker 100. For example, the temperature of the liquid can be less than about 37 degrees Celsius, such as less than 30 degrees Celsius, or less than 20 degrees Celsius.

In still other embodiments, the temperature necessary to cause a particular shape-memory polymer material of tissue cavity marker 100 to transition to its permanent state can be approximately equal to human body temperature, such that simply deploying tissue cavity marker 100 in cavity 303 causes tissue cavity marker 100 to transition to its permanent state. In these embodiments, no liquid need be injected. In veterinary applications, the body temperature can be a body temperature of a particular animal type or species.

Figure 3E:
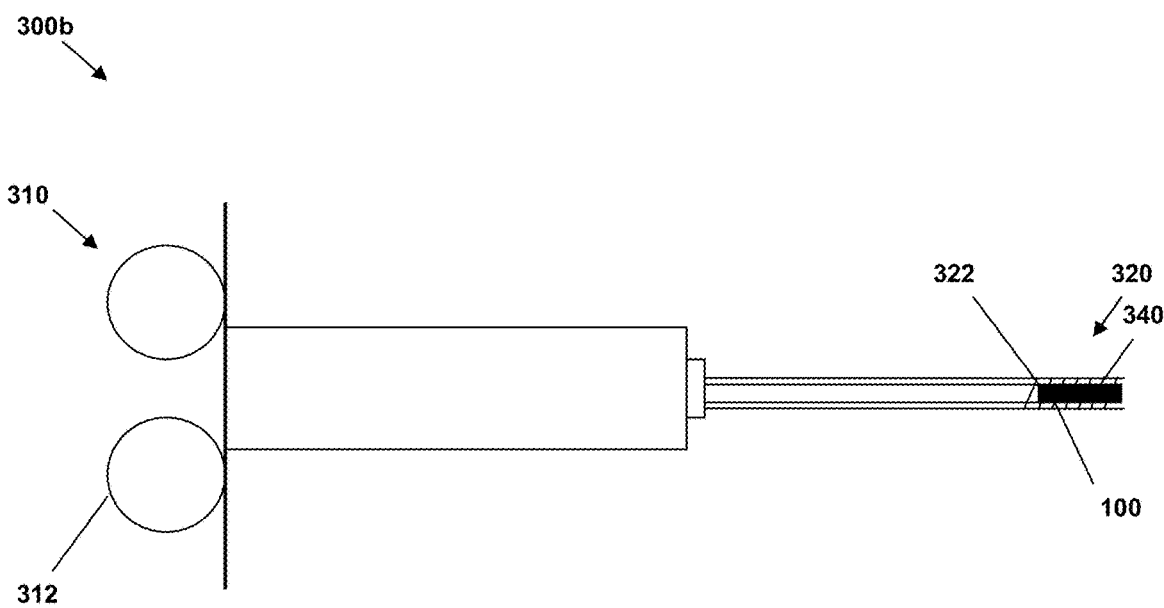
FIG. 3E depicts a delivery device loaded with a shape-memory polymer tissue cavity marker according to yet another embodiment.

Other transition techniques also can be used in temperature-effected transition embodiments. For example, and referring to FIG. 3E, delivery device 300b can comprise a heater coil 340 or other device at or near distal delivery end 320. Heater coil 340b or other device can be activated once distal delivery end 320 is positioned in or at cavity 303 and before tissue cavity marker 100 is deployed, such that tissue cavity marker 100 is heated by heater coil 340b or other device as it is deployed from distal delivery end 320. For example, the tip of distal delivery end 320 can be advanced to a distal edge of cavity 303, and tissue cavity marker 100 can be transformed as it is deployed from distal end aperture 322 as distal delivery end 320 and delivery device 300 are retracted. In another example, distal delivery end 320 is advanced to a proximal edge of cavity 303, and tissue cavity marker 100 is transformed as it is deployed by being pushed into cavity 303, such as by control system 312, which also can control activation and deactivation of heater coil 340. In embodiments comprising heater coil 340 or some other transformation-effecting element, distal end aperture 322 may be located at another position along distal delivery end 320, such as closer to proximal control end 310, in order to be positioned relative to heater coil 340 and provide sufficient time or distance for tissue cavity marker 100 to interact with heater coil 340 to be transformed during deployment.

Heater coil 340b can be replaced with a cooling device in embodiments in which temperatures less than human body temperature are needed. In another embodiment, a balloon can be inserted into tissue cavity marker 100 in cavity 300, and the balloon can be filled with heated saline or other fluid to cause tissue cavity marker 100 to transition to its permanent state. The balloon then can be drained and withdrawn. In yet another embodiment, tissue cavity marker 100 can be deployed in cavity 303 within a balloon. The balloon then can be filled with heated saline or another material to cause tissue cavity marker 100 to transition to its permanent state. The balloon then can be drained and withdrawn while leaving tissue cavity marker 100 in place in cavity 303.

In still other embodiments, a laser, ultrasound, or other temperature-altering technique can be used to cause tissue cavity marker 100 to transition from its temporary state to its permanent state within cavity 303. Finally, other suitable techniques can be used in embodiments in which the shape-memory polymer material of tissue cavity marker 100 is responsive to a stimulus other than temperature, such as those identified elsewhere herein or others appreciated by those of ordinary skill in the art.

In any embodiment, regardless of the particular stimulus necessary to cause tissue cavity marker 100 to transition to its permanent state in cavity 303, the stimulus can be provided by delivery device 300 or some other, separate device. For example, in the embodiment in which heated saline is delivered to cavity 303, the saline can be delivered via delivery device 300, and delivery also can be controlled by control system 312, such as in the embodiment of FIG. 3D. Alternatively, the saline can be delivered by a separate syringe or other device, while distal delivery end 320 of delivery device 300 is still in place or after tissue cavity marker 100 has been deployed and distal delivery end 320 retracted from incision 301. The particular temperature or technique used can depend on cavity site and type, potential beneficial effect(s) provided to the tissue margins of cavity 303, procedure characteristic, physician preference or experience, or some other factor.

Additionally, in embodiments in which a heated or cooled liquid is injected to cause tissue cavity marker 100 to transition to its permanent state, a material other than saline can be used. For example, some medicament or fluid having a therapeutic or beneficial effect can be used. Instead of a liquid, another material such as a gel or a gas also can be used in embodiments.

Upon transition to its permanent state, tissue cavity marker 100 will remain in cavity 303, and distal delivery end 320 can be retracted and removed. Because tissue cavity marker 100 generally will be left in cavity 303 indefinitely, incision 301 can be closed. As previously mentioned, tissue cavity marker 100, and thereby cavity 303, can be located on X-ray or other images via radiopaque markers 120, 220 (see FIGS. 1A, 1B, 2A and 2B) and will not migrate from cavity 303 because tissue cavity marker 100 holds them in place. Over time, new tissue will grow into cavity 303 and around tissue cavity marker 100, and tissue cavity marker 100 will resorb, leaving only radiopaque markers 120 or 220 behind in the tissue now filling former cavity 303.

While the examples discussed herein include tissue cavity marker 100 loaded in its temporary state into distal end aperture 322 of distal delivery end 320 of delivery device 300, in other embodiments tissue cavity marker 100 can be loaded into distal end aperture 322 in its permanent state. In some embodiments, the deployed state of tissue cavity marker 100 within a tissue cavity is then the temporary state of tissue cavity marker 100. In other embodiments, tissue cavity marker 100 can be induced to transition from the permanent state to the temporary state after loading into distal end aperture 322 of delivery device 300 and before deployment in a tissue cavity, such that tissue cavity marker 100 is induced to transition back to the permanent state during or after deployment for residence in the tissue cavity.

Figure 4:
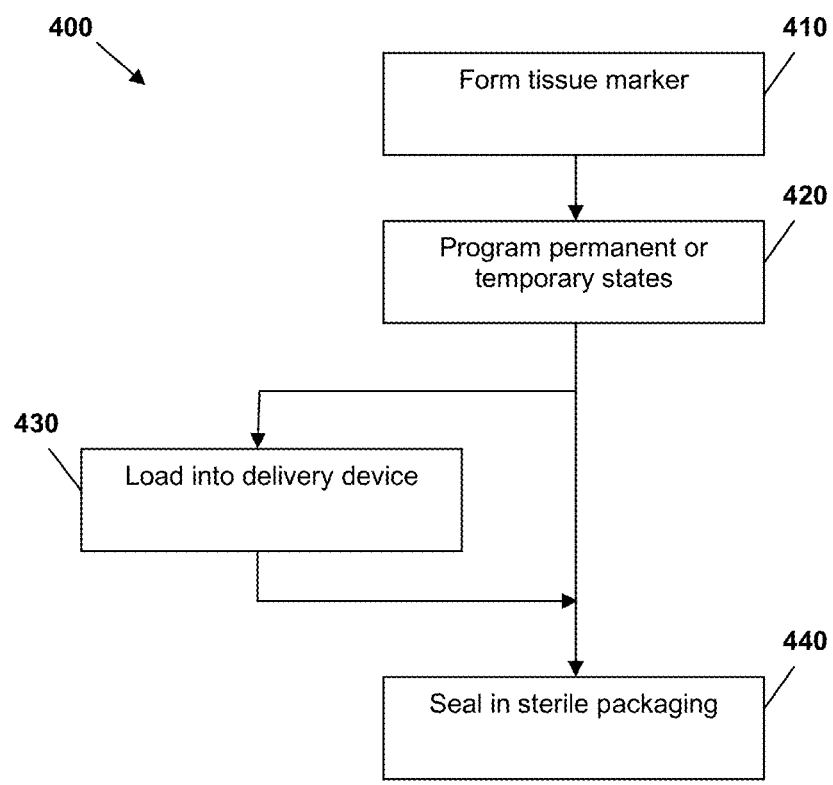
FIG. 4 is a flowchart of a method of forming a shape-memory polymer tissue cavity marker according to an embodiment.

Referring to FIG. 4, a method 400 of providing a tissue cavity marker, such as tissue cavity marker 100 or tissue cavity marker 200, is depicted. At 410, a tissue cavity marker is formed, such as from a shape-memory polymer material. Forming the tissue cavity marker can include selecting a permanent shape of tissue cavity marker, and cutting, molding, three-dimensionally printing, or otherwise manipulating the shape-memory polymer material to enable the desired complex, three-dimensional permanent shape. At 420, the tissue cavity marker can be programmed with its permanent or temporary state. This can include straining the material (e.g., subjecting it to a temperature while forming it into a particular desired shape) to cause the permanent or temporary state shape to be retained in the "memory" of the material. Optionally, at 430, the tissue cavity marker can be put into its temporary state and loaded into a delivery device or a portion of a delivery device. At 440, the loaded delivery device or the individual tissue cavity marker can be sealed in sterile packaging. In various embodiments, the order of activities depicted in FIG. 4 can be changed, additional activities can be inserted, and depicted activities can be omitted.

Embodiments of the tissue cavity markers discussed herein provide advantages with respect to conventional tissue markers. For example, the shape-memory effect of the material from which the tissue cavity marker can be formed enables the tissue cavity marker to be delivered via an incision with a length or other dimension that is smaller than a diameter or other dimension of the tissue cavity marker in its permanent state. The shape, dimensions and other characteristics of the tissue cavity maker in various embodiments also can be selected to provide a snug fit of the tissue cavity marker within a cavity, thereby providing a secure frame or support structure for the radiopaque marker(s) coupled to the tissue cavity marker and inhibiting the radiopaque markers from migrating within the cavity. The frame of the tissue cavity marker and its ability to expand three-dimensionally within the cavity also provides for a plurality of radiopaque markers to be used to more completely define the margins of the cavity. Once new tissue has grown into the cavity and around the radiopque markers, the markers are less likely to migrate, such that the tissue cavity marker can be formed from a bioabsorbable material and need not be removed by another surgical procedure. This can increase patient comfort and recovery, reduce expense and eliminate procedures (as well as the likelihood for complications) by eliminating the need for a second procedure to remove the tissue cavity marker. Additionally, the ability to customize the permanent and temporary shapes of the tissue cavity marker means it can be used in a variety of different places and procedures, including but not limited to breast tissue biopsies and lumpectomies as well as other tissue biopsy sites.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A tissue cavity marker for delivery to a tissue cavity via a minimally invasive surgical incision, the tissue cavity marker comprising:
   a transformative body having a first three-dimensional shape in a permanent state and a second three-dimensional shape different from the first three-dimensional shape in a temporary state, the transformative body comprising a shape-memory polymer material and being automatically transformable between the temporary state for delivery to a tissue cavity and the permanent state for residence within the tissue cavity by application of a stimulus; and
   at least one radiopaque marker comprising a structure defining an aperture through which a portion of the transformative body passes.

2. The tissue cavity marker of claim 1, wherein the shape-memory polymer material comprises a bioabsorbable material.

3. The tissue cavity marker of claim 2, wherein the bioabsorbable material comprises at least one of poly-lactic acid (PLA), poly-L-lactide (PLLA), poly-l-glycolic acid (PLGA), or polycaprolactone (PCL).

4. The tissue cavity marker of claim 1, wherein at least two dimensions of the first three-dimensional shape are greater than a length of the minimally invasive surgical incision.

5. The tissue cavity marker of claim 4, wherein the length of the minimally invasive surgical incision is less than 1 centimeter (cm).

6. The tissue cavity marker of claim 5, wherein the length of the minimally invasive surgical incision is about than 6 millimeters (mm).

7. The tissue cavity marker of claim 6, wherein a diameter of the first three-dimensional shape is in a range of 10 mm to 30 mm, and wherein a diameter of the second three-dimensional shape is less than about 6 mm.

8. The tissue cavity marker of claim 1, wherein the at least one radiopaque marker comprises titanium or nonferromagnetic stainless steel.

9. The tissue cavity marker of claim 1, wherein the stimulus is a temperature change.

10. The tissue cavity marker of claim 9, wherein a temperature of the temperature change is approximately equal to human body temperature.

11. The tissue cavity marker of claim 9, wherein a temperature of the temperature change is greater than 40 degrees Celsius.

12. The tissue cavity marker of claim 11, wherein the temperature of the temperature change is between 60 degrees Celsius and 80 degrees Celsius.

13. The tissue cavity marker of claim 1, wherein at least one dimension of the tissue cavity marker in the permanent state is approximately equal to or greater than a dimension of the tissue cavity.

14. The tissue cavity marker of claim 1, wherein the transformative body is a unitary body.

15. The tissue cavity marker of claim 1, wherein the tissue cavity marker physically interacts with at least a portion of a margin of the tissue cavity in the permanent state.

16. The tissue cavity marker of claim 1, wherein the transformative body consists of the shape-memory polymer material.

17. A tissue cavity marking system for delivering a tissue cavity marker to a tissue cavity via a minimally invasive surgical incision, the system comprising:

a delivery device comprising a control mechanism at a proximal end and a tissue cavity marker aperture at a distal end, the control mechanism operable in use to deploy a tissue cavity marker from the tissue cavity marker aperture; and at least one tissue cavity marker comprising:

a transformative body having a first three-dimensional shape in a permanent state and a second three-dimensional shape different from the first three-dimensional shape in a temporary state, the transformative body comprising a shape-memory polymer material and being automatically transformable between the temporary state for delivery to a tissue cavity and the permanent state for residence within the tissue cavity by application of a stimulus, and at least one radiopaque marker comprising a structure defining an aperture through which a portion of the transformative body passes.

18. The tissue cavity marking system of claim 17, wherein one of the at least one tissue cavity markers is preloaded in the tissue cavity marker aperture.

19. The tissue cavity marking system of claim 18, further comprising a sterile package in which the delivery device and the one of the at least one tissue cavity marker preloaded in the tissue cavity marker aperture are sealed.

20. The tissue cavity marking system of claim 17, wherein the delivery device comprises a fluid aperture, and wherein a fluid delivered to the tissue cavity via the fluid aperture causes the transformative body to automatically transform from the temporary state to the permanent state.

21. The tissue cavity marking system of claim 17, wherein the shape-memory polymer material comprises a bioabsorbable material.

22. The tissue cavity marking system of claim 17, wherein a diameter of the tissue cavity marker aperture is less than a length of the minimally invasive surgical incision.

23. The tissue cavity marking system of claim 22, wherein the length of the minimally invasive surgical incision is less than 1 centimeter (cm).

24. The tissue cavity marking system of claim 23, wherein the stimulus is a temperature change.

* * * * *